US006488634B1

(12) United States Patent
Rapoport et al.

(10) Patent No.: US 6,488,634 B1
(45) Date of Patent: **\*Dec. 3, 2002**

(54) METHOD AND APPARATUS FOR OPTIMIZING THE CONTINUOUS POSITIVE AIRWAY PRESSURE FOR TREATING OBSTRUCTIVE SLEEP APNEA

(75) Inventors: David M. Rapoport, New York, NY (US); Robert G. Norman, New Windsor, NY (US)

(73) Assignee: New York University, New York, NY (US)

( * ) Notice: Subject to any disclaimer, the term of this patent is extended or adjusted under 35 U.S.C. 154(b) by 80 days.

This patent is subject to a terminal disclaimer.

(21) Appl. No.: 09/602,158

(22) Filed: Jun. 22, 2000

Related U.S. Application Data

(63) Continuation of application No. 08/644,371, filed on May 10, 1996, now Pat. No. 6,299,581, which is a continuation of application No. 08/482,866, filed on Jun. 7, 1995, now Pat. No. 5,535,739, which is a division of application No. 08/246,964, filed on May 20, 1994, now Pat. No. 5,490,502, which is a continuation-in-part of application No. 07/879,578, filed on May 7, 1992, now Pat. No. 5,335,654.

(51) Int. Cl.$^7$ .............................................. A61B 5/00
(52) U.S. Cl. .................................. 600/538; 128/204.23
(58) Field of Search ................................ 600/529, 538; 128/204.23

(56) References Cited

U.S. PATENT DOCUMENTS

| | | | |
|---|---|---|---|
| 4,365,636 A | 12/1982 | Barker | 128/716 |
| 4,440,177 A | 4/1984 | Anderson et al. | |
| 4,655,213 A | 4/1987 | Rapoport et al. | 128/205.25 |
| 4,686,974 A | 8/1987 | Sato et al. | 128/204.23 |
| 4,944,310 A | 7/1990 | Sullivan | |
| 5,065,756 A | 11/1991 | Rapoport | 128/204.18 |
| 5,107,831 A | 4/1992 | Halpern et al. | |
| 5,134,995 A | 8/1992 | Gruenke et al. | 128/204.23 |

(List continued on next page.)

FOREIGN PATENT DOCUMENTS

EP    0 504 725 A2    9/1992

OTHER PUBLICATIONS

Dupuis, "Ventilators—Theory and Clinical Application", The C.V. Mosby Co., 1986 pp. 107–117.

Southworth et al., "Digital Computation and Numerical Methods", McGraw–Hill, Inc. 1965, pp. 6–10.

Primary Examiner—Robert L. Nasser
(74) Attorney, Agent, or Firm—Fulwider Patton Lee & Utecht, LLP

(57) ABSTRACT

In the treatment of obstructive sleep apnea, a method and apparatus are disclosed for optimizing the controlled positive pressure to minimize the flow of air from a flow generator while still ensuring that flow limitation in the patient's airway does not occur. In particular, the invention relates to a breathing device and method of use to adjust a controlled positive pressure to the airway of a patient by detecting flow limitation from analysis of an inspiratory flow waveform. Once the presence of flow limitation has been analyzed, the system determines an action to take for adjustment of the controlled positive pressure. The pressure setting is raised, lowered or maintained depending on whether flow limitation has been detected and on the previous actions taken by the system. The preferred breathing apparatus consists of a flow generator, a flow sensor, an analog to digital converter, a microprocessor, and a pressure controller, a patient supply hose, a nasal fitting, and, optionally, a pressure transducer. Using the method of the present invention, the microprocessor adjusts the air pressure in the patient supply hose when flow limitation is detected in the airway of the patient.

20 Claims, 13 Drawing Sheets

U.S. PATENT DOCUMENTS

| | | | |
|---|---|---|---|
| 5,148,802 A | 9/1992 | Sanders et al. | 128/204.18 |
| 5,199,424 A | 4/1993 | Sullivan et al. | 128/204.18 |
| 5,203,343 A | 4/1993 | Axe et al. | 128/725 |
| 5,239,995 A | 8/1993 | Estes et al. | 128/204.23 |
| 5,335,654 A * | 8/1994 | Rapoport | 128/204.23 |
| 5,433,193 A | 7/1995 | Sanders et al. | 128/204.18 |
| 5,458,137 A | 10/1995 | Axe et al. | 128/204.23 |
| 5,522,382 A * | 6/1996 | Sullivan et al. | 128/204.23 |
| 5,645,053 A | 7/1997 | Remmers et al. | 128/204.23 |
| 5,704,345 A | 1/1998 | Berthon-Jones | 128/204.23 |

* cited by examiner

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

|  | | CURRENT BREATH | | |
|---|---|---|---|---|
|  | | NO FLOW LIM. | INTERMEDIATE | FLOW LIMITED |
| PREVIOUS BREATH(S) | NO FLOW LIM. | 1.00–1.25 | 1.00–1.10 | 1.00–1.25 |
| | INTERMEDIATE | 1.00–0.90 | 1.00 | 1.00–0.90 |
| | FLOW LIMITED | 1.00–0.75 | 1.00–0.90 | 1.00–0.75 |

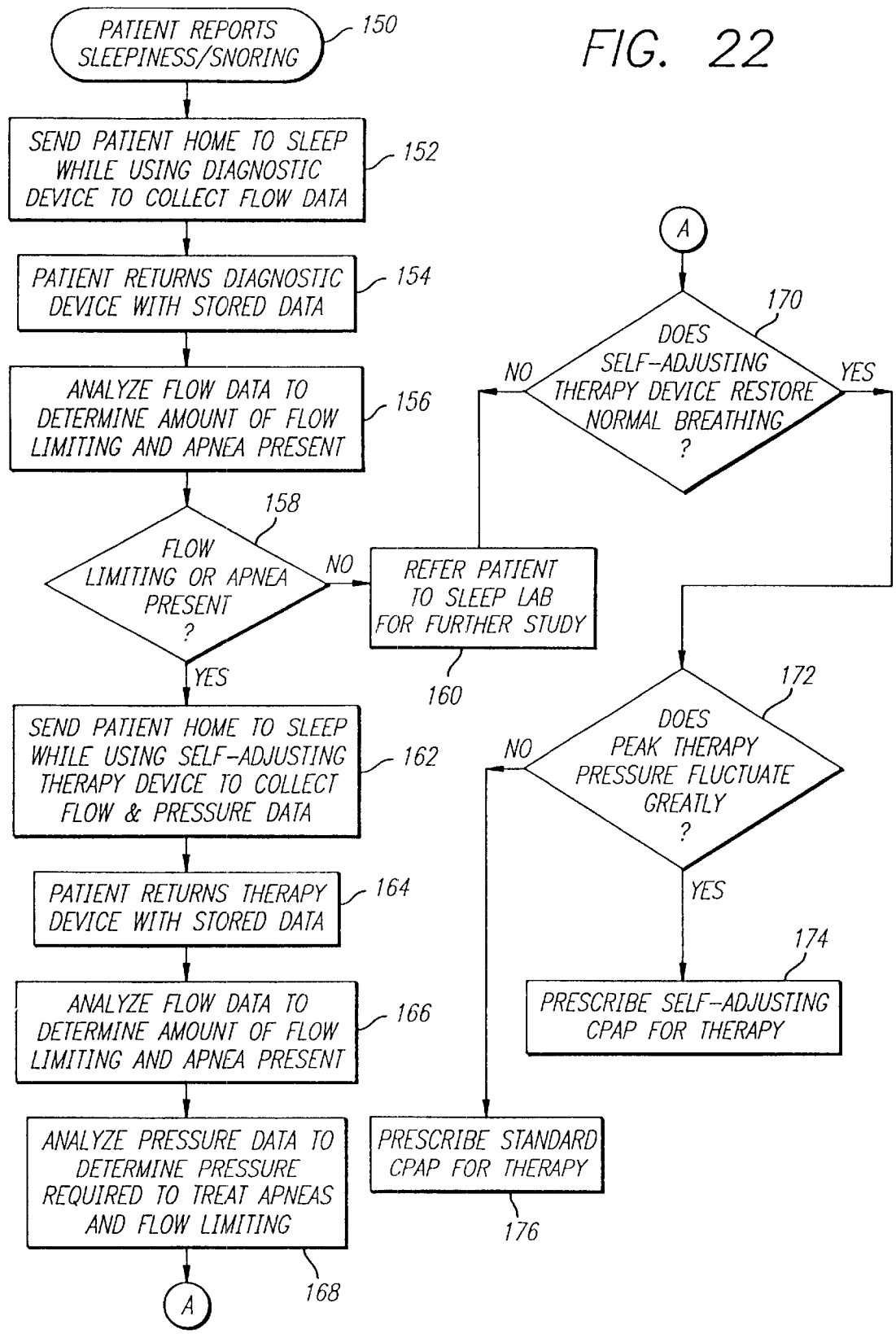

METHOD AND APPARATUS FOR OPTIMIZING THE CONTINUOUS POSITIVE AIRWAY PRESSURE FOR TREATING OBSTRUCTIVE SLEEP APNEA

CROSS-REFERENCE TO RELATED APPLICATION

This application is a continuation of U.S. application Ser. No. 08/644,371 filed May 10, 1996 (U.S. Pat No. 6,299,581), which is a continuation of U.S. application Ser. No. 08/482,866, filed Jun. 7, 1995 (U.S. Pat. No. 5,535,739), which is a division of U.S. application Ser. No. 08/246,964, filed May 20, 1994 (U.S. Pat. No. 5,490,502), which is a continuation-in-part of U.S. application Ser. No. 07/879,578, filed May 7, 1992 (U.S. Pat. No. 5,335,654), the contents of which are hereby incorporated herein by reference.

BACKGROUND OF THE INVENTION

This invention relates to a method and apparatus for adjusting the positive airway pressure of a patient to an optimum value in the treatment of obstructive sleep apnea, and more particularly to a breathing device which maintains constant positive airway pressure and method of use which analyzes an inspiratory flow waveform to titrate such a pressure value.

Obstructive sleep apnea syndrome (OSAS) is a well recognized disorder which may affect as much as 1–5% of the adult population. OSAS is one of the most common causes of excessive daytime somnolence. OSAS is most frequent in obese males, and it is the single most frequent reason for referral to sleep disorder clinics.

OSAS is associated with all conditions in which there is anatomic or functional narrowing of the patient's upper airway, and is characterized by an intermittent obstruction of the upper airway occurring during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia and sleep disruption associated with the apneas and arousals from sleep.

The pathophysiology of OSAS is not fully worked out. However, it is now well recognized that obstruction of the upper airway during sleep is in part due to the collapsible behavior of the supraglottic segment during the negative intraluminal pressure generated by inspiratory effort. Thus, the human upper airway during sleep behaves as a Starling resistor, which is defined by the property that the flow is limited to a fixed value irrespective of the driving (inspiratory) pressure. Partial or complete airway collapse can then occur associated with the loss of airway tone which is characteristic of the onset of sleep and may be exaggerated in OSAS.

Since 1981, continuous positive airway pressure (CPAP) applied by a tight fitting nasal mask worn during sleep has evolved as the most effective treatment for this disorder, and is now the standard of care. The availability of this non-invasive form of therapy has resulted in extensive publicity for apnea and the appearance of large numbers of patients who previously may have avoided the medical establishment because of the fear of tracheostomy. Increasing the comfort of the system, which is partially determined by minimizing the necessary nasal pressure, has been a major goal of research aimed at improving patient compliance with therapy. Various systems for the treatment of obstructive sleep apnea are disclosed, for example, in "Reversal of Obstructive Sleep Apnea by Continuous Positive Airway Pressure Applied Through The Nares", Sullivan et al, Lancet, 1981, 1:862–865; and "Reversal of The 'Pickwickian Syndrome' By Long-Term Use of Nocturnal Nasal-Airway Pressure"; Rapaport et al., New England Journal of Medicine, Oct. 7, 1982. Similarly, the article "Induction of upper airway occlusion in sleeping individuals with subatmospheric nasal pressure", Schwartz et al, Journal of Applied Physiology, 1988, 64, pp. 535–542, discusses various polysomnographic techniques. Each of these articles are hereby incorporated herein by reference.

Despite its success, limitations to the use of nasal CPAP exist. These mostly take the form of discomfort from the mask and the nasal pressure required to obliterate the apneas. Systems for minimizing the discomfort from the mask are disclosed, for example, in U.S. Pat. No. 4,655,213, Rapaport et al, and U.S. Pat. No. 5,065,756, Rapaport, as well as in "Therapeutic Options For Obstructive Sleep Apnea", Garay, Respiratory Management, July/August 1987, pp. 11–15; and "Techniques For Administering Nasal CPAP", Rapaport, Respiratory Management, July/August 1987, pp. 18–21 (each being hereby incorporated herein by reference). Minimizing the necessary pressure remains a goal of the preliminary testing of a patient in the sleep laboratory. However, it has been shown that this pressure varies throughout the night with sleep stage and body position. Furthermore, the therapeutic pressure may both rise or fall with time in patients with changing anatomy (nasal congestion/polyps), change in weight, changing medication or with alcohol use. Because of this, most sleep laboratories currently prescribe the setting for home use of nasal CPAP pressure based upon the single highest value of pressures needed to obliterate apneas during a night of monitoring in the sleep laboratory. Retesting is often necessary if the patient complains of incomplete resolution of daytime sleepiness, and may reveal a change in the required pressure.

SUMMARY OF THE INVENTION

The invention is therefore directed to a method and apparatus, in a system for the treatment of obstructive sleep apnea, for optimizing the controlled positive pressure to thereby minimize the flow of air from a flow generator while still ensuring that flow limitation in the patient's airway does not occur. In particular, the invention relates to a breathing device and method of use to adjust a controlled positive pressure to the airway of a patient by detecting flow limitation from analysis of an inspiratory flow waveform.

In accordance with the invention, an apparatus for the treatment of obstructive sleep apnea is provided, comprising a source of air, and means for directing an air flow from said source to a patient. This part of the system may be of the type disclosed, for example, in U.S. Pat. No. 5,065,756. In addition, means are provided for sensing the waveform of said airflow, to detect deviations therein that correspond to flow limitation in the air supplied to the patient. Such deviations may be, for example, deviations from a substantially sinusoidal waveform, flattening, or the presence of plateaus, in the portions of the waveform corresponding to inspiration of the patient. In response to such variations in said airflow, the system of the invention increases or decreases the pressure to the patient.

In accordance with the method of the invention, the controlled positive pressure to the patient is increased in response to the detection of flow waveform portions corresponding to flow limitations in the patient airway. Such pressure increases may be effected periodically. Similarly, the controlled positive pressure may be periodically decreased in the absence of such flow limitation. The system may be provided with a program that periodically decreases the controlled positive pressure in the absence of detection of flow limitations in the patient airway, and that periodically increases the pressure in the presence of detection of such flow limitations.

The method for determining whether to increase or decrease the controlled positive pressure is comprised of several steps. The first step is to detect the presence of a valid breath and store an inspiratory waveform of that breath for further analysis. Next, the waveform of the stored breath is analyzed regarding its shape for presence of flow limitation. Whether flow limitation is present is in part determined by flow limitation parameters calculated from the shape of the waveforms of the current breath and of the immediately preceding breath. Once the presence of flow limitation has been analyzed, the system determines an action to take for adjustment of the controlled positive pressure. The pressure setting is raised, lowered or maintained depending on whether flow limitation has been detected and on the previous actions taken by the system.

The preferred breathing device or apparatus consists of a flow generator, such as a variable-speed blower, a flow sensor, an analog to digital converter, a microprocessor, and a pressure controller, such as a blower motor speed control circuit, a patient connection hose, a nasal coupling, such as a nose mask or similar fitting, and, optionally, a pressure transducer. Alternative patient circuits may be employed, such as those disclosed in U.S. Pat Nos. 4,655,213 and 5,065,756. For example, a positive pressure breathing gas source may be connected to a pressure control valve proximate the breathing gas source and connected to a nasal mask having a venting means.

In the preferred embodiment, the blower supplies air through the flow sensor to the patient via a hose and nasal coupling. The microprocessor obtains the flow waveform from the digitized output of the flow sensor. Using the method of the present invention described herein, the microprocessor adjusts the speed of the blower via the motor control circuit to change the air pressure in the patient supply hose. A pressure transducer may be provided to measure the actual pressure in the patient hose. In addition, the microprocessor may store measured pressure and flow waveform values in its data memory to provide a history for real-time or off-line processing and analysis.

Other features and advantages of the present invention will become apparent from the following detailed description, taken in conjunction with the accompanying drawings, which illustrate, by way of example, the principles of the invention.

BRIEF DESCRIPTION OF THE DRAWING

FIG. 22 is a flow diagram illustrating a method of diagnosing and treating a patient in accordance with the invention.

DETAILED DISCLOSURE OF THE INVENTION

FIGS. 1–5 illustrate the waveforms of flow from a CPAP generator, obtained during the testing of a patient, in sleep studies. In these tests, the patient was wearing a CPAP mask connected to an air source, in the manner illustrated in U.S. Pat. No. 5,065,765. Each of these tests illustrate an epoch of 30 seconds, with the vertical lines depicting seconds during the tests. FIGS. 1–5 depict separate sweeps that were taken from 1 to 2 minutes apart, and with different pressures from the source of air.

Figure 1:
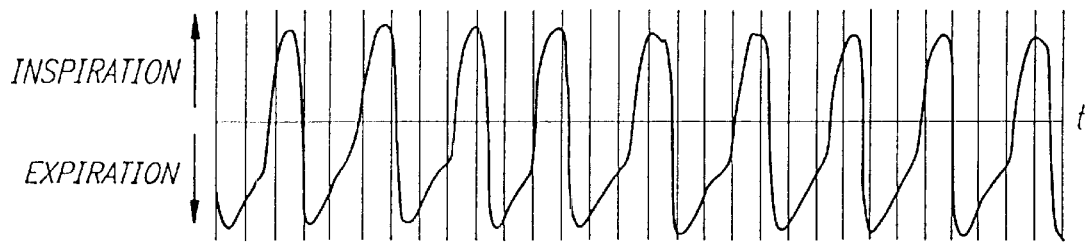
FIG. 1 is the waveform of the airflow of a 30 second epoch to a sleeping patient from a CPAP generator, with a CPAP pressure of 10 cm $H_2O$.

FIG. 1 illustrates a "normal" waveform, in this instance with a CPAP pressure of 10 cm $H_2O$. This pressure was identified as corresponding to apnea free respiration. It is noted that this waveform, at least in the inspiration periods, is substantially sinusoidal. The waveforms of FIGS. 2–5 illustrate that, as the controlled positive pressure is lowered, a predictable index of increasing collapsibility of the airway occurs, prior to the occurrence of frank apnea, periodic breathing or arousal.

Figure 2:
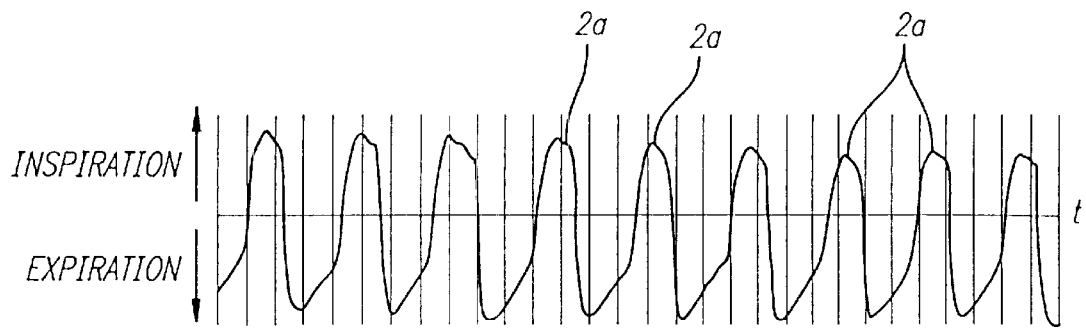
FIG. 2 is the waveform of the airflow of a 30 second epoch to the sleeping patient of FIG. 1, from a CPAP generator, with a CPAP pressure of 8 cm $H_2O$.
Figure 3:
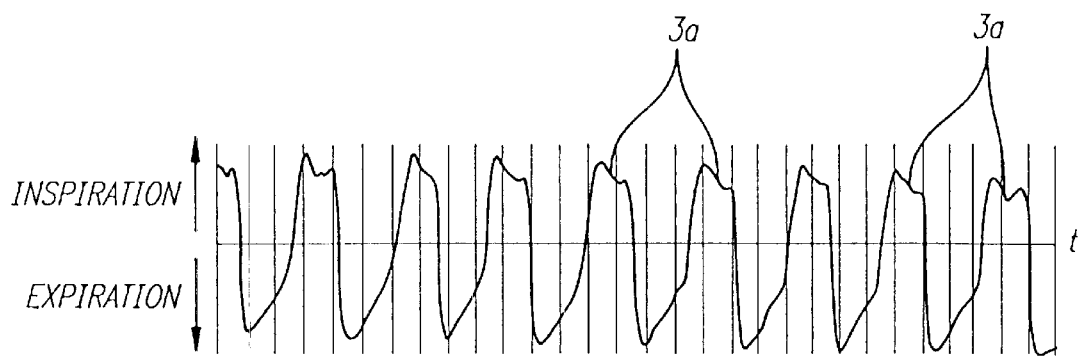
FIG. 3 is the waveform of the airflow of a 30 second epoch to the sleeping patient of FIG. 1, from a CPAP generator, with a CPAP pressure of 6 cm $H_2O$.
Figure 4:
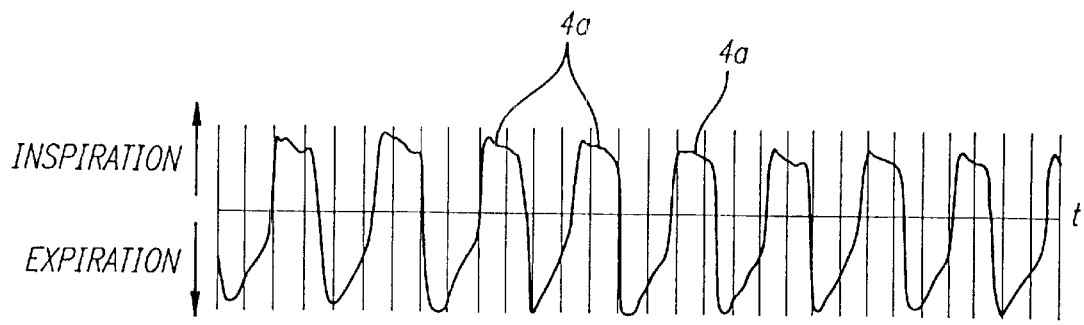
FIG. 4 is the waveform of the airflow of a 30 second epoch to the sleeping patient of FIG. 1, from a CPAP generator, with a CPAP pressure of 4 cm $H_2O$.
Figure 5:
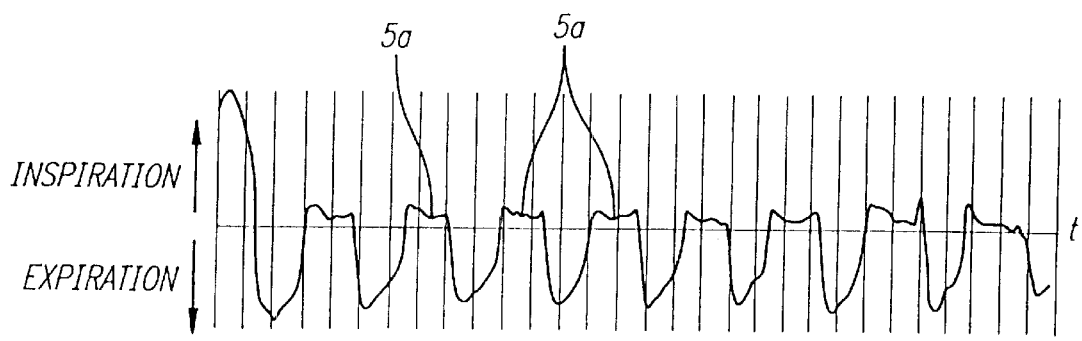
FIG. 5 is the waveform of the airflow of a 30 second epoch to the sleeping patient of FIG. 1, from a CPAP generator, with a CPAP pressure of 2 cm $H_2O$.

When the CPAP pressure was decreased to 8 cm $H_2O$, as illustrated in FIG. 2, a partial flattening of the inspiratory flow waveform, at regions 2a, began to occur. This flattening became more definite when the controlled positive pressure was decreased to 6 cm H$_2$O, as illustrated by the reference numeral 3a in FIG. 3. The flattening becomes even more pronounced, as seen at the regions 4a of FIG. 4, when the controlled positive pressure was reduced to 4 cm. Reductions in the CPAP pressure from the pressure of apnea free respiration resulted in snoring by the patient. When the controlled positive pressure was reduced to 2 cm H$_2$O, as illustrated in FIG. 5, there was virtually zero inspiratory flow during the inspiratory effort, as seen at the portions 5a. Shortly after the recording of the waveform of FIG. 5, the patient developed frank apnea and awakened.

Figure 6:
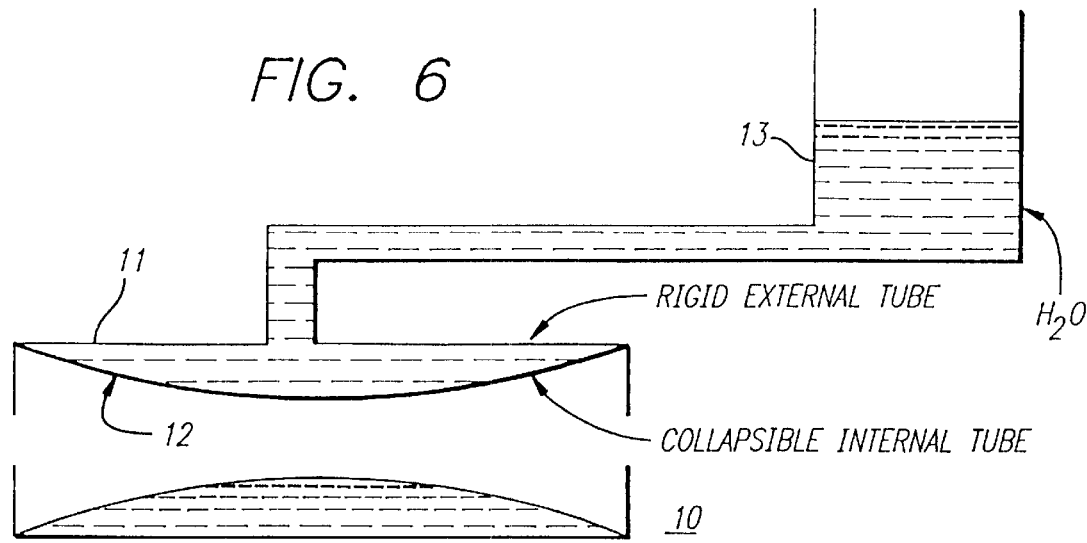
FIG. 6 is a simplified cross sectional view of a Starling resistor.
Figure 7:
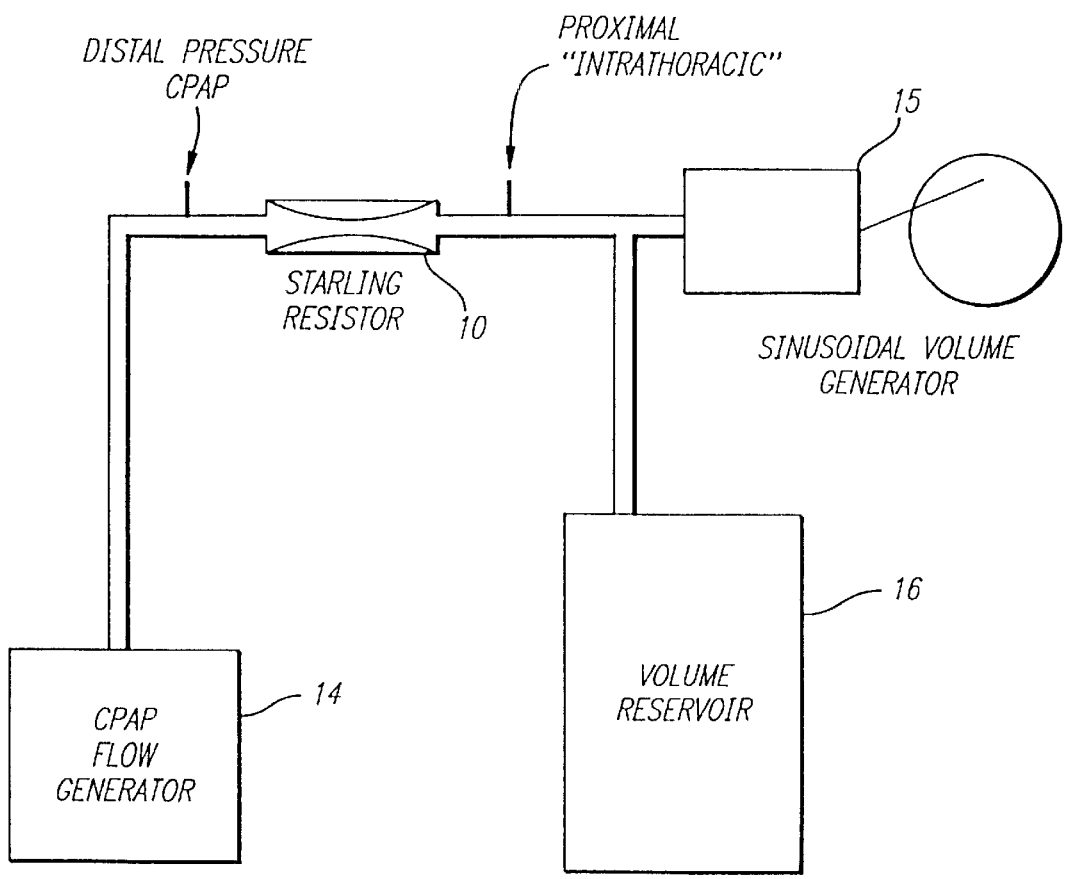
FIG. 7 is a simplified block diagram of an experimental setup employing a Starling resistor.

The waveforms of FIGS. 1–5 are consistent with experiments wherein the collapsible segment of the air passage is simulated by a Starling resistor. A Starling resister 10, as illustrated in FIG. 6, is comprised of a rigid external tube 11 supporting an internal collapsible tube 12. Water is introduced into the space between the outer tube 11 and inner tube 12, for example, through a tube connected to a water column 13 of adjustable height to enable variation of the external pressure applied to the collapsible tube 12. With reference to FIG. 7, in this experiment, a commercial CPAP flow generator 14 is coupled to the "distal" end of the Starling resistor 10, and "respiration" is simulated by a sinusoidal pump 15 coupled to the "proximal" or "intrathoracic" end of the resistor 10. A volume reservoir 16 is coupled to the proximal end of the Starling resistor, to provide a capacitive volume that prevents excessive negative pressure from developing during total system occlusion (apnea).

Figure 8:
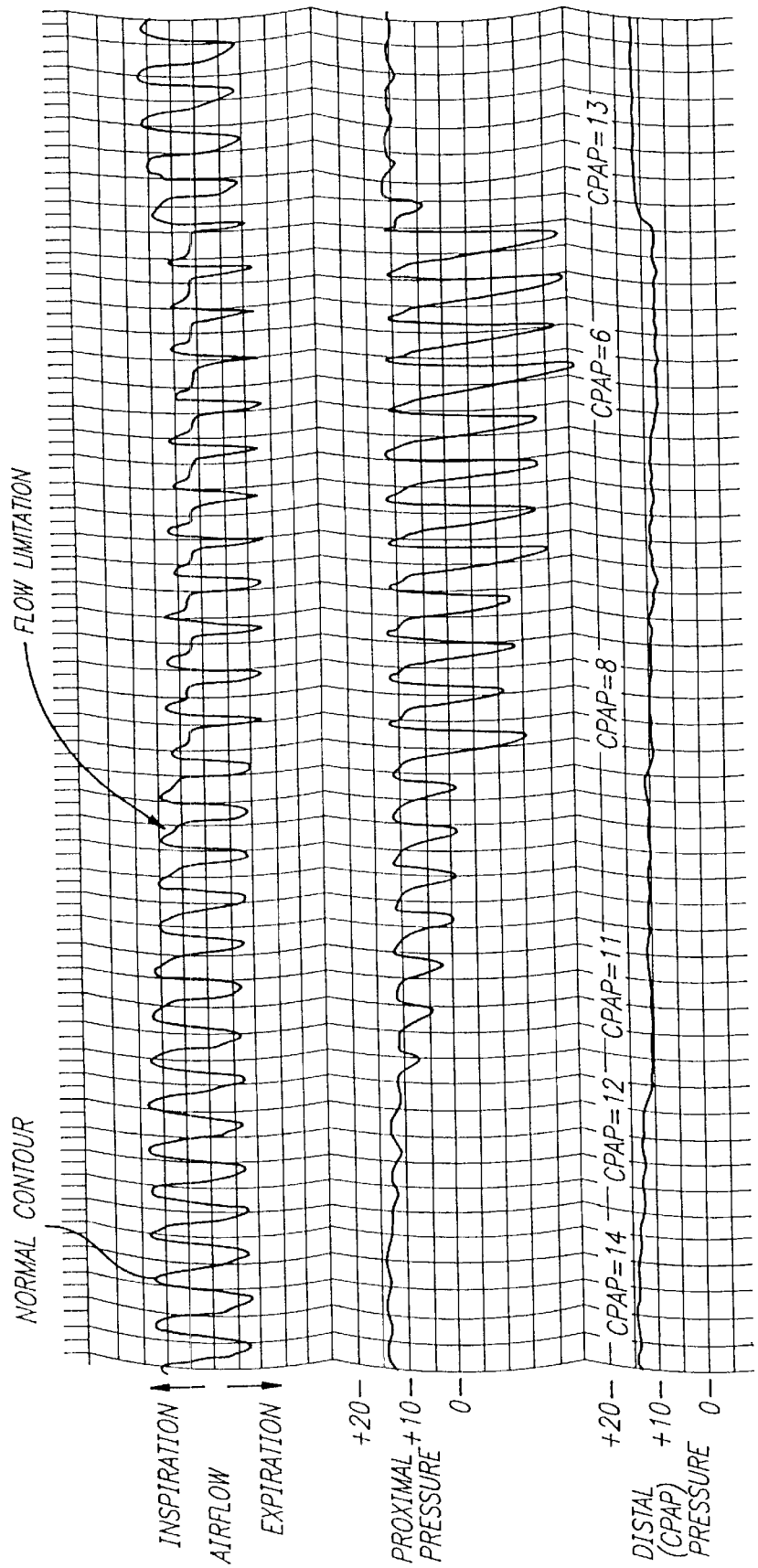
FIG. 8 is a set of waveforms generated by use of the setup of FIG. 7.

The flow tracing of FIG. 8 was generated using the system of FIG. 6, with the level of water in the column 13 set between 5 and 15 cm H$_2$O. The airflow from the CPAP flow generator was started at a pressure of 14 cm H$_2$O, then sequentially decreased to 12 cm, 11 cm, 8 cm and 6 cm H$_2$O, and finally returned to 13 cm H$_2$O. In FIG. 8, the upper curve shows the waveform of the airflow, the middle curve shows the waveform of the proximal pressure (i.e., at the port of the sinusoidal generator 15, and the lower curve illustrates the CPAP pressure. The gradations at the top of FIG. 8 denote seconds. FIG. 8 thus reflects the large increase in resistance across the Starling resistor, and mimics the increasingly negative intrathoracic pressure routinely seen in patients with an apnea, snoring and any increased upper airway resistance syndrome.

In accordance with the invention, waveforms of the flow of air, of the type illustrated in FIGS. 1–5, are employed in order to control the flow of air from a CPAP generator, to thereby minimize the flow of air from the generator while still ensuring that flow limitation does not occur.

Figure 9:
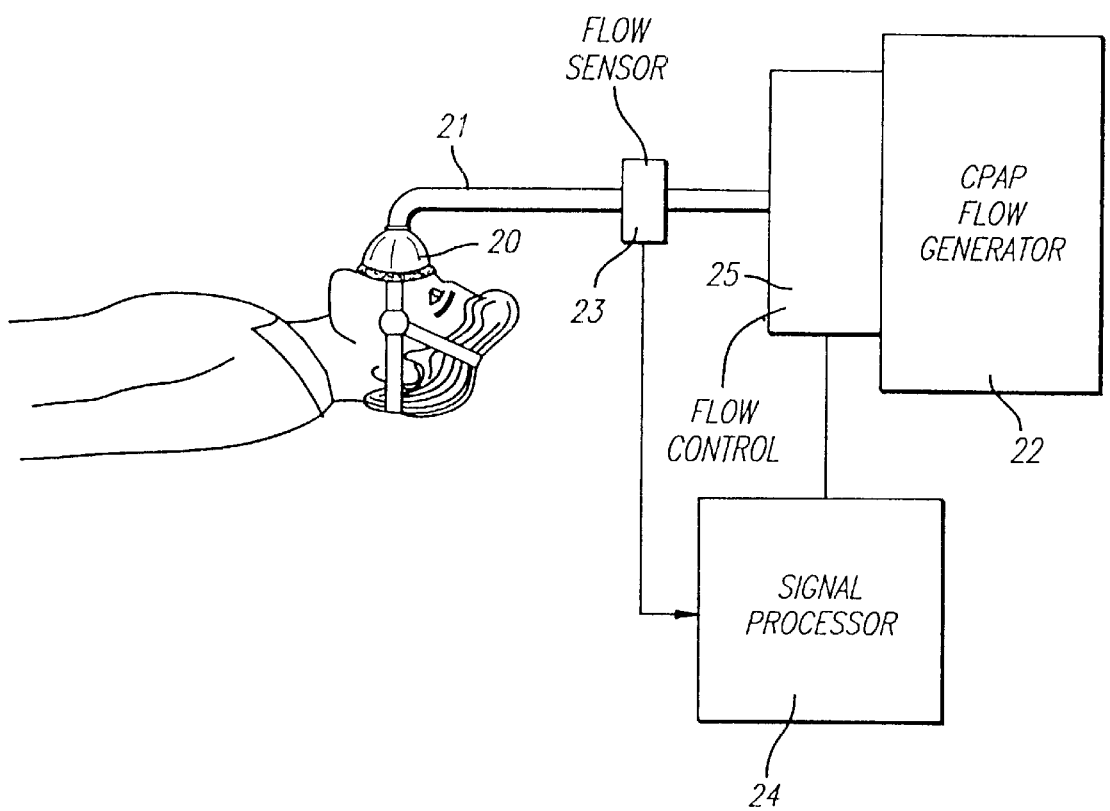
FIG. 9 is a simplified block diagram of a system in accordance with the invention.

In one embodiment of the invention, as illustrated in FIG. 9, a CPAP mask 20 is connected via tube 21 to receive air from a CPAP flow generator 22. These elements may be of the type disclosed in U.S. Pat. No. 5,065,756, although the invention is not limited thereto, and any conventional CPAP system may alternatively be employed. A conventional flow sensor 23 is coupled to the tube 21, to provide an electric output signal corresponding to the waveform of the airflow in the tube 21. This signal is applied to a signal processor 24, which detects the existence in the waveforms of conditions that indicate flow limitation. The signal processor 24 outputs a signal to a conventional flow control 25 for controlling the pressure applied by the flow generator to the tube 21. It is of course apparent that, depending upon the type of flow generator 22, the signal processor may directly control the flow generator, instead of controlling a flow control device 25.

Figure 10:
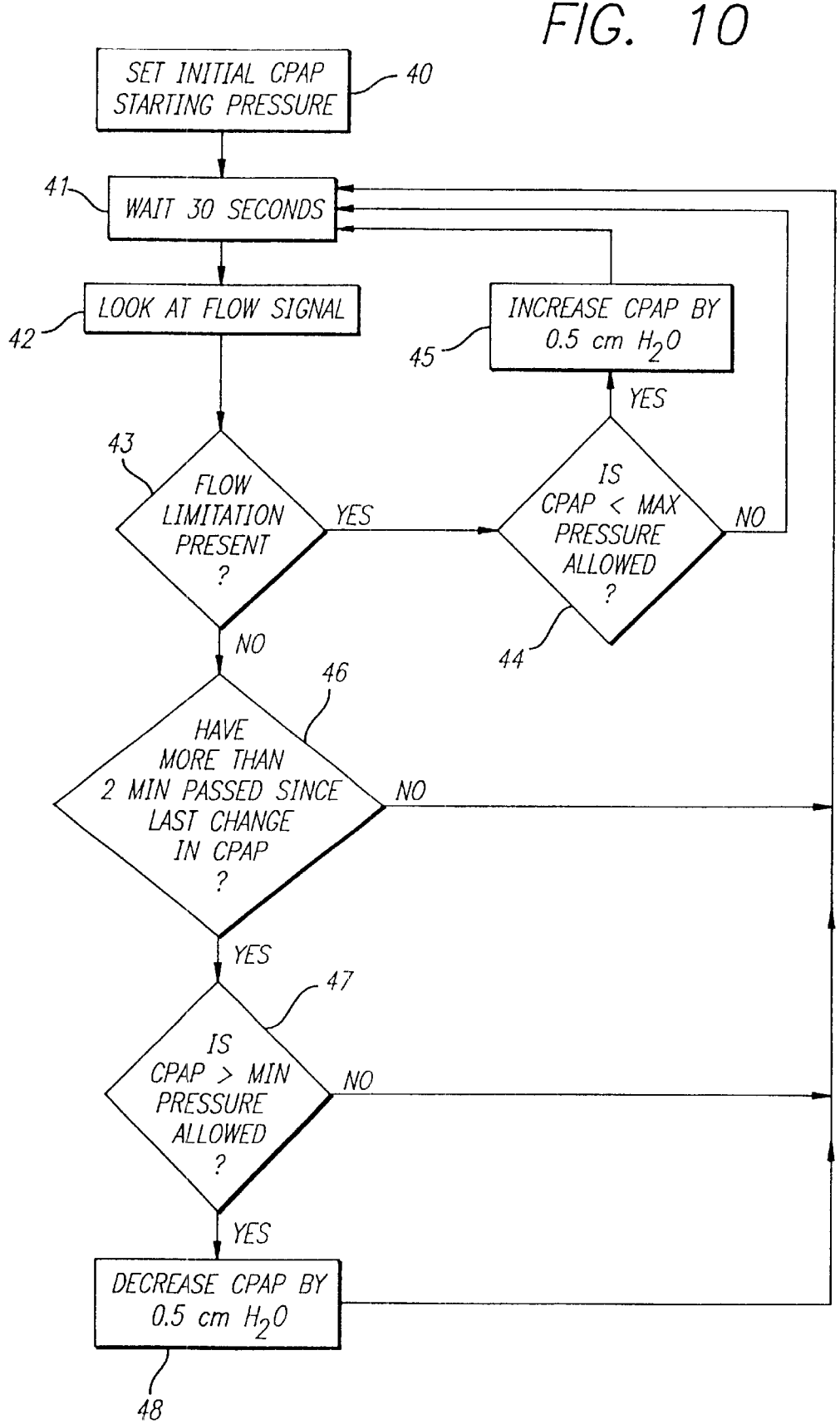
FIG. 10 is a flow diagram illustrating one technique for adjusting the CPAP pressure, in accordance with the invention.

One method for adjusting the CPAP pressure in accordance with the invention is illustrated in FIG. 10. After the CPAP mask has been fitted to a patient and the CPAP generator has been connected to the mask (step 40), the CPAP pressure is set at a starting pressure. This pressure is a pressure at which flow limitation for the patient does not occur. After a settling period of about 30 seconds (step 41), the flow signal is analyzed (step 42).

If it is determined that flow limitation has occurred (step 43) and that the CPAP pressure is less than the maximum allowed (step 44), then the CPAP pressure is increased by 0.5 cm H$_2$O (step 45) and the method returns to the settling step 41 for further processing. If at the pressure comparing step 44 the pressure was not less than the maximum allowed CPAP pressure, then the method returns to the settling step 41 without increasing the CPAP pressure.

If it was determined that a flow limitation was not present (step 43), then a determination is made (step 46) whether a predetermined time has elapsed following the last change in the CPAP pressure. The predetermined time may be, for example, two minutes. If the predetermined time has not elapsed, then the method returns to the settling period step 41. If the predetermined minimum time has elapsed, it is determined whether the CPAP pressure is greater than the minimum allowed pressure (step 47). If it is greater than the minimum allowed pressure, then the CPAP pressure is decreased by 0.5 cm H$_2$O (step 48), and the method returns to the settling step 41. Otherwise, the returns to the settling step 41 without decreasing the CPAP pressure.

While the above described example of the method of the invention employed CPAP pressure change steps of 0.5 cm H$_2$O, it is apparent that the invention is not limited to pressure changes of this magnitude. In addition, the pressure changes may not necessarily be equal throughout the range of adjustment.

Similarly, the flow limitation determination step 43 may involve any of a number of waveform analysis procedures. For example, the signal corresponding to the airflow waveform may be differentiated in the portions thereof corresponding to inspiration. A markedly peaked result from such differentiation indicates the presence of flow limitation, as is evident from an analysis of the differentials of the waveforms of FIGS. 1–5. Alternatively, the waveform may be analyzed for the presence of harmonics of the cyclic rate of the waveform in the inspiration period thereof, since the presence of a significant amplitude of harmonics of the cyclic rate (i.e., the breathing rate) indicates the present of a waveform indicative of flow limitation. It is evident that analyses of this type may be effected by conventional hardware or software. The invention, however, is not limited to the above specific techniques for determining divergence of the waveform from the normal non-flow limited waveform to a waveform indicating the presence of flow limitation.

The optimizing method for determining whether to increase or decrease the controlled positive pressure is comprised of several steps. The first step is to detect the presence of a valid breath and store data values corresponding to an inspiratory flow waveform of that breath for further analysis. Alternatively, flow data values may be stored for the entire breath. Next, the stored breath waveform is analyzed regarding its shape for presence of flow limitation. Whether flow limitation is present is in part determined by flow limitation parameters calculated from the shape of the waveforms of the current breath and of the immediately preceding breath. Once the presence of flow limitation has been analyzed, the system determines an action to take for adjustment of the controlled positive pressure. The pressure setting is raised, lowered or maintained depending on whether flow limitation has been detected and on the previous actions taken by the system.

The optimizing method has several input parameters which are used in the determination of the action to be taken during the automatic adjustment mode. For example, the initial controlled positive pressure, or "start value," must be available for use when power-on occurs in the breathing device. Similarly, the method requires a "therapeutic level" of controlled positive pressure to return to whenever an exception condition is detected, such as high constant flow. If the method cannot determine with reasonable certainty that breathing is present, it returns the controlled positive pressure to the prescribed therapeutic level. Also, a "low limit" and a "high limit" are required to determine the minimum and maximum controlled positive pressure level the system will generate when operating in the automatic adjustment mode. The method cannot cause the controlled positive pressure to exceed the maximum or minimum limits of pressure.

Figure 11:
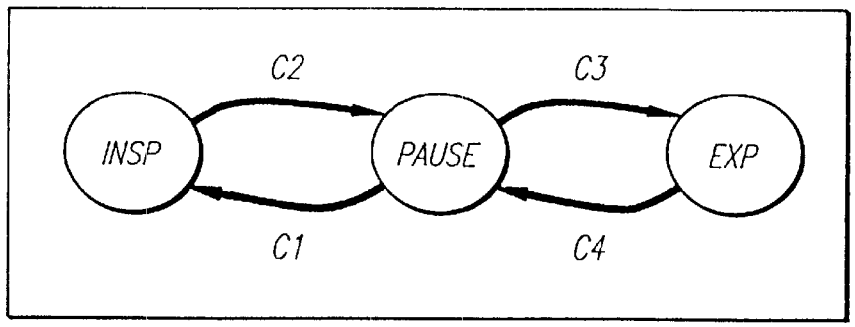
FIG. 11 is a transition diagram of a three phase state machine with states corresponding to the phases of respiration.

The method for optimizing the controlled positive pressure will now be described in more detail. The first step in the optimizing method is the detection of a valid breath. A valid breath is determined by a cyclical fluctuation in the respiratory signal superimposed on the constant system leak. This detection is implemented using a three phase state machine with states corresponding to the phases of patient respiration. The transition diagram of this state machine is shown in FIG. 11 and described below. As is well known in the art, the logic for the state machine may be programmed into the software of a microprocessor or similar computer hardware.

The total flow signal present within the positive pressure flow generator is used as a basis for the breath detection method steps. The breath detection method produces measured data corresponding to the inspiratory flow waveform. Similarly, the breath detection method estimates the constant leak flow and determines several breath description parameters, which are described in more detail below. These measured and calculated data form the input to the flow limitation detection step of the optimizing method.

Figure 12:
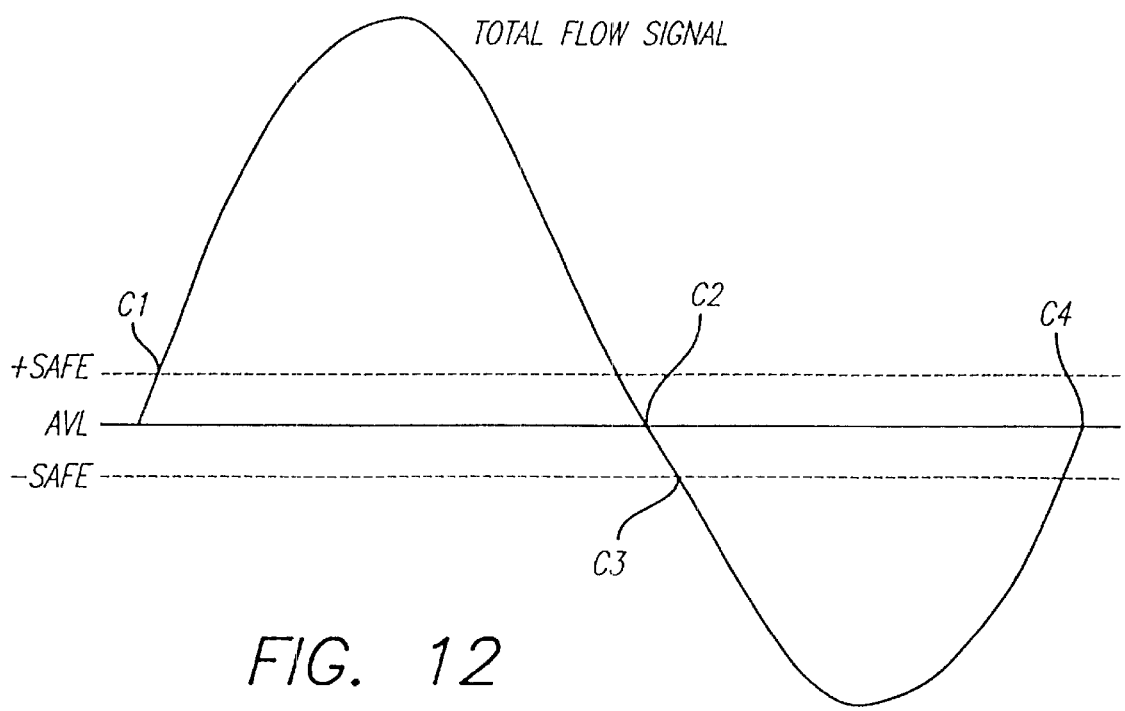
FIG. 12 is a plot of a total flow signal depicting the state transitions shown in FIG. 11.

As shown in FIG. 12, the state machine uses the actual flow signal from the controlled positive pressure source and two derived reference flow signals to determine state transitions. The first state of the state machine is the inspiratory state (INSP). The second state is the expiratory state (EXP). In the third state (PAUSE), the state machine is in transition from INSP to EXP, or from EXP to INSP. The onset of an INSP state defines the beginning of a valid breath. Likewise, the onset of the next INSP state defines the end of a valid breath.

The four state changes (C1, C2, C3, and C4), are shown in FIGS. 11 and 12. The first state change (C1), is determined by the state machine moving from the PAUSE state to the INSP state. This transition denotes the completion of the preceding breath, which is processed before proceeding to the next breath. The data collected and calculated for a breath is discarded if it does not meet certain preprogrammed minimal time and amplitude criteria. The first transition occurs whenever the system is in PAUSE and the total flow signal exceeds the sum of a calculated average leak value (ALV) plus a calculated safety value (SAFE) used as a dead-band. In addition, the derivative of the flow signal must be greater than a minimum set value. This criteria enables the system to differentiate between the onset of inspiration and mere changes in flow leakage in the breathing device.

The average leak value (ALV) is a calculated running average of the actual flow signal modified to reflect the possible absence of an expiratory signal. The estimate of the average leak flow is updated during each of the three phases INSP, EXP, PAUSE. The safety reference value (SAFE) is the level of fluctuation in the flow signal which is considered noise. This is calculated as an average of a fraction of the peak flow in each breath. Alternatively, the total flow signal may be first differentiated and then integrated to remove the constant DC offset component (leak flow) and the value of ALV set to zero. Also, the method steps may be applied to the estimated flow signal output of a CPAP generator (which has the constant leak value subtracted out) and the ALV set equal to zero.

In the second transition (C2), the machine state changes from the INSP state to the PAUSE state. This transition occurs when the system is in the INSP state and the total flow signal drops below the ALV. In the next transition (C3), the state machine changes from the PAUSE state to the EXP state. This transition occurs when the system is in the PAUSE state and the total flow signal drops below the ALV minus SAFE reference value. Lastly, the state machine transitions from the EXP state to the PAUSE state (C4). This transition occurs when the system is in the EXP state and the total flow signal rises above the ALV.

The system performs certain calculations during the phase states (INSP, EXP, PAUSE) and phase transitions (C1, C2, C3, C4). During the inspiratory phase (INSP), the system accumulates and stores measured data of total flow, e.g., in a flow buffer. Also during the inspiratory phase, the system determines the maximum inspiratory flow value and the maximum derivative value for the total flow signal. During the expiratory phase (EXP), the system determines the maximum expiratory flow value.

During the first transition (C1), the system determines whether the current breath meets the valid criteria for time and size. At the same time, the system calculates a new safety value (SAFE) as a fraction of the breath size. During the second transition (C2), the system determines the inspiratory time and calculates the running average of the maximum derivative. During the fourth transition (C4), the system calculates the expiratory time.

Figure 13:
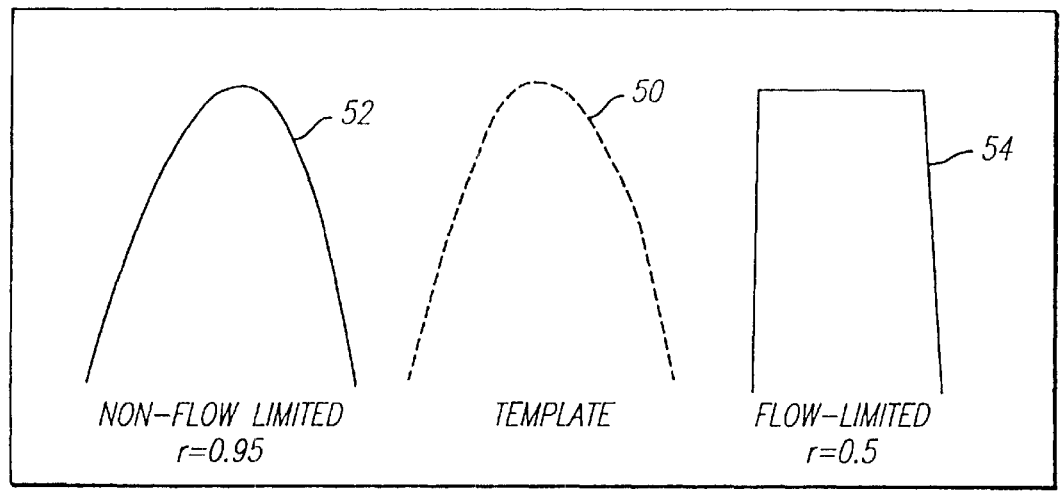
FIG. 13 is a set of waveforms used to correlate an inspiratory wave with a sinusoidal half wave.

The determination of the degree of flow limitation present is based on four shape detection parameters, the sinusoidal index, the flatness index, the respiratory effort index and the relative flow magnitude index. The sinusoidal parameter or index is calculated as a correlation coefficient of the actual total inspiratory flow wave (filtered) to a reference sinusoidal half wave. As shown in FIG. 13, a half sinusoidal template 50 that matches the timing and amplitude of the actual total inspiratory flow data is compared to the actual total inspiratory flow data, for example, using a standard Pearson product moment correlation coefficient. This correlation coefficient is an index ranging from 1 (sinusoidal or not flow limited) to 0 (not sinusoidal).

A typical non-flow limited shape 52 and flow limited shape 54 are shown in FIG. 13 for comparison. The comparison may be applied to an entire inspiratory waveform (halfwave) or to the mid-portion whose shape is most characteristic of either normal or flow limited breaths. The preferred section of the inspiratory waveform is that which is most discriminate between normal and flow limited behavior, for example, the mid-portion of the inspiratory flow data.

Figure 14:
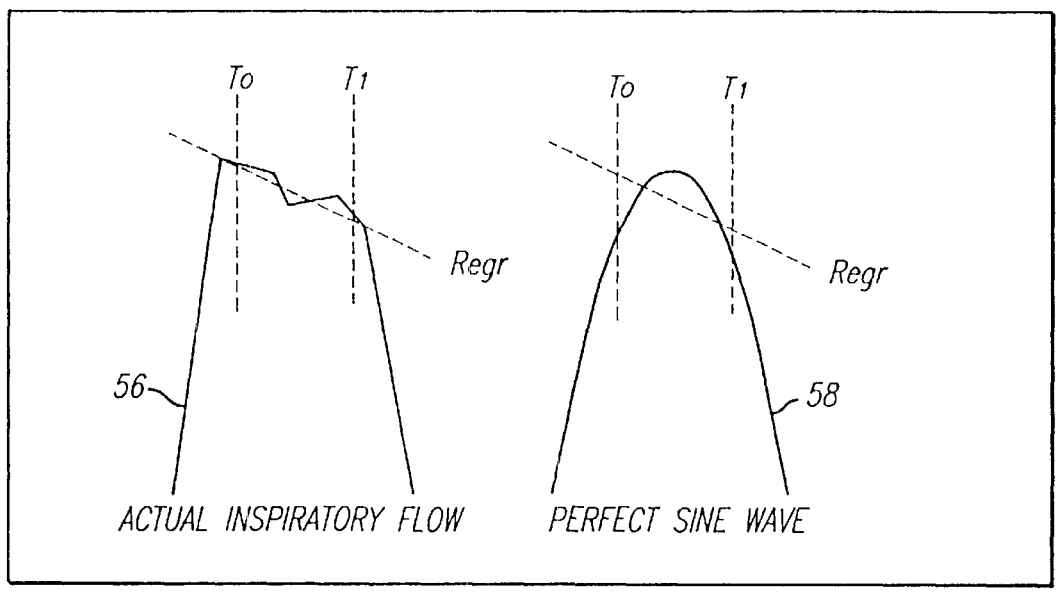
FIG. 14 shows a regression fit to a mid-third of an inspiratory wave and to a sinusoidal half wave.

The flatness parameter is a representation of the degree of flatness (or curvature) present in the total inspiratory flow signal. This index is calculated as a variance ratio of the actual signal around a calculated regression line (actual curvature) and an ideal half sinusoidal signal around the same regression line (curvature standard). As shown in FIG. 14, the regression (REGR) is calculated using the mid-portion of the inspiratory flow data 56, for example, from the end of the first third of the inspiratory portion of the breath T0 to the beginning of the last third of the inspiratory portion of the breath T1. This regression is calculated using least squares techniques. The variance of the actual total inspiratory flow data 56 around this regression line is then calculated for the mid-portion of the inspiration. Likewise the variance of the mid-portion of a pure half sinusoidal template with matching period and amplitude around the regression line is also calculated. The ratio of these two variances produces the flatness parameter or index which ranges from 1 (sinusoidal) to 0 (flat).

Figures 15, 16:
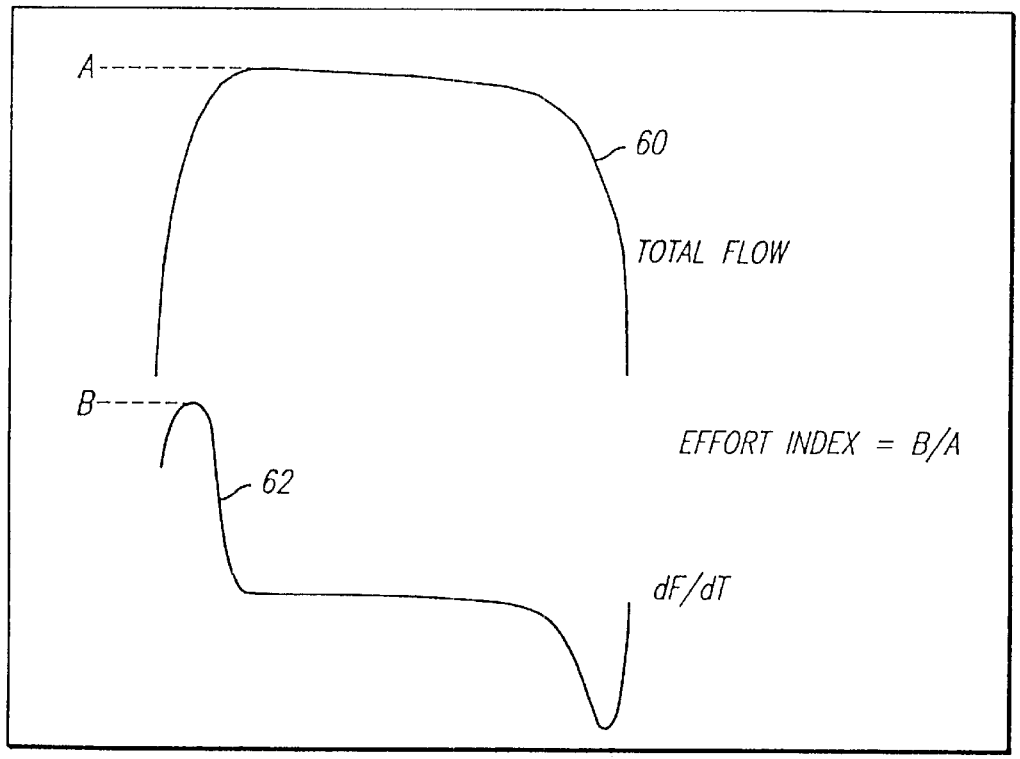
FIG. 15 is a plot of a total flow signal and a derivative of an inspiratory waveform depicting a respiratory effort index.
FIG. 16 contains a table of the probability factors used to modify the flow limitation parameters.

The system calculates the respiratory effort index as the ratio of peak derivative (rate of change of flow with respect to time) of the early inspiratory waveform to the peak flow value of the inspiratory waveform. FIG. 15 shows the peak (A) of the total inspiratory flow waveform as plotted against the peak (B) of the waveform for the derivative of the inspiratory flow. The ratio of the peak values (B/A) is also known as the "effort index." This parameter is useful to detect flow limitation in a patient, because an increased respiratory effort is manifested in an increased slope of the inspiratory flow waveform.

The system calculates the relative flow magnitude index as the peak flow of the inspiratory flow waveform minus the peak flow of the previous inspiratory flow waveforms showing flow-limitation divided by the running average of the peak flows of the non-limited breaths minus the average of the flow-limited breaths. This parameter is calculated as:

MINMAX=FLOW−MIN/MAX−MIN

WHERE:

FLOW is the peak flow rate of the current breath

MIN is an average of the peak flow of the 20 most recent flow limited breaths.

MAX is an average of the peak flow of the 20 most recent normal breaths.

This results in a parameter or index which ranges from 0 (flow limited) to 1 (normal).

The four shape detection parameters described above are calculated for the current valid breath and the values are combined using a mathematical function, such as a logistic regression sum. Similarly, weighting factors may be used, wherein the weight given to one or more of the indexes may be zero, positive or negative. The combined values provide a flow limitation parameter which has a value between 0 and 1 that characterizes the likelihood that the current breath has a shape characteristic of flow-limitation. The value of the flow limitation parameter is further modified based on the value of the preceding breaths' flow limitation parameters used as a prior probability, allowing calculation of a posterior probability.

The four shape detection parameters (sinusoidal index, flatness index, respiratory effort index and relative flow magnitude index) are used in a mathematical function to determine a likelihood of flow limitation using a logistic regression equation:

$$p = \frac{e^{f(x)}}{1 + e^{f(x)}}$$

Where "p" is the probability of flow limitation; "e" is the base of the natural logarithms; X1, X2, X3 and X4 are the shape detection parameters; B0, B1, B2, B3 and B4 are the weighting coefficients (which may include zero) and $f(x) = B_1 + B_0 {}^* X_1 + B_2 {}^* X_2 + B_3 {}^* X_3 + B_4 {}^* X_4.$ The probability of flow limitation (p) has a limited range from 0 (flow limitation) to 1 (normal) and is valid for all values of the function f(x).

FIG. 16 shows the prior probability factor which is applied to the initial value of the flow limitation parameter calculated from the shape parameters to yield a final value for the current valid breath. The prior probability factors are used to modify the flow limitation parameter based on previous breath's value for flow limitation. The underlined value is an estimate of the best value to be used as a multiplicative or additive to the index. Thus, the flow limitation parameter is made more important when other flow limited breaths have been detected. Similarly, the index is made less "flow limited" if the present occurrence is an isolated incident.

If the flow limitation parameter is between 1 and a predetermined normal reference value, e.g., 0.65–0.8, then the breath is classified as "normal." If the flow limitation parameter is between 0 and a predetermined flow limited reference value, e.g., 0.4, then the breath is classified as "flow limited." If the flow limitation parameter is between the normal and flow limited reference values, then the breath is classified as "intermediate."

As each valid breath is identified, its likelihood of being flow limited is calculated. The flow limitation parameter approaches a value of 1 for a normal breath and 0 for a flow limited breath. In the method of the present invention, a decision is made as to whether to adjust the controlled positive pressure. This decision is dependent on three factors:

1) the value of the flow limitation parameter for the current breath;

2) the value of the flow limitation parameters in the preceding interval (several breaths);

3) whether the controlled positive pressure has been adjusted (and the direction) in the preceding interval of time.

Generally, if flow limitation is detected, the controlled positive pressure will be raised. Similarly, if no flow limitation is detected for an interval of time, then the controlled positive pressure is lowered to test for the development of flow limitation. The desired effect of the method of the present invention is for the controlled positive pressure to remain slightly above or below the optimal positive pressure despite changes in the optimal therapeutic level of pressure which may occur over time.

Figure 17:
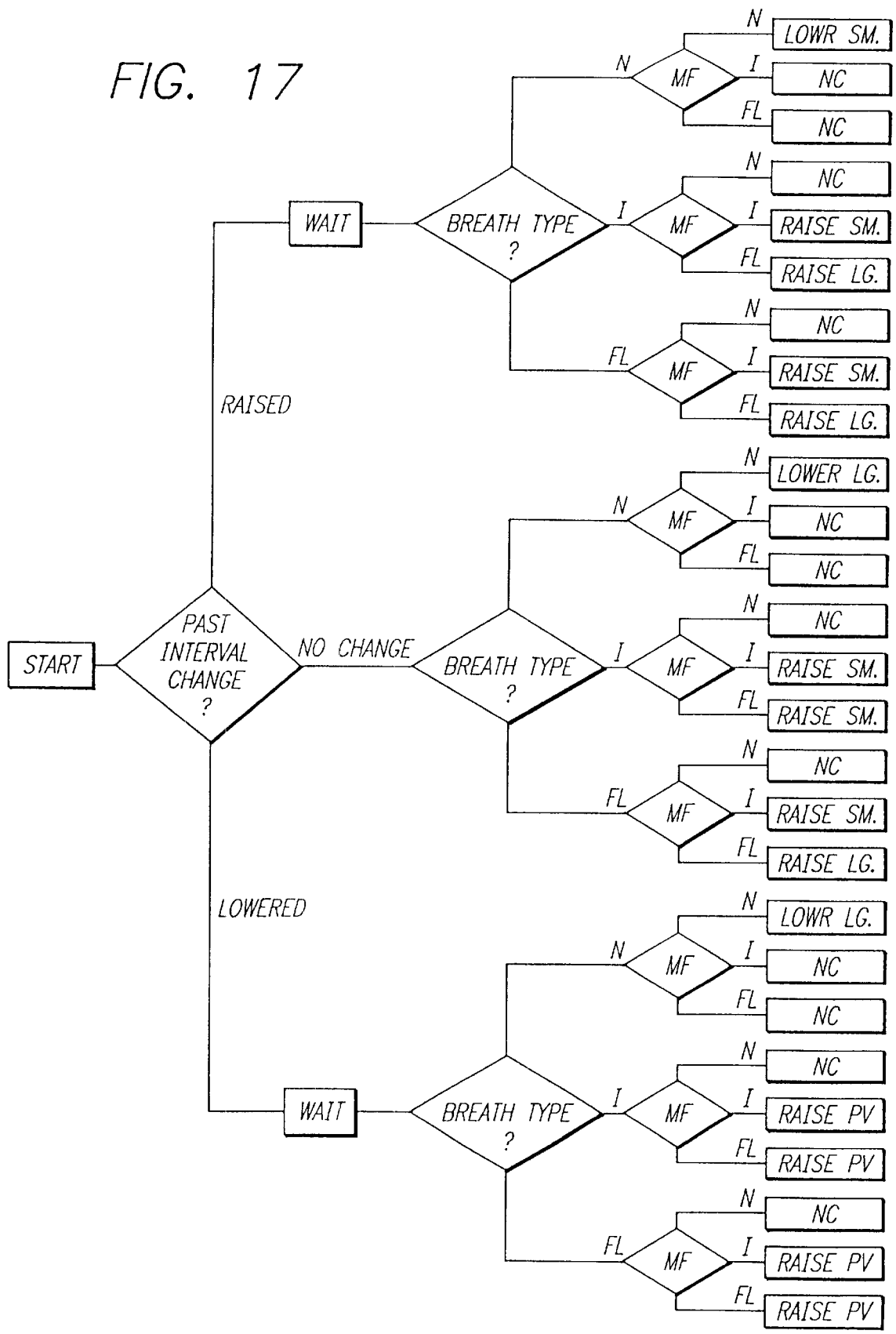
FIG. 17 is a flow diagram illustrating one technique for determining whether and how to adjust the controlled positive pressure, in accordance with the invention.

As shown in the flow chart of FIG. 17, the method of the present invention uses a decision tree to determine whether to change the controlled positive pressure to the airway of the patient. The steps of the method may be programmed in the software of a microprocessor or similar computer. As part of the decision process, the system calculates a time weighted majority function (MF) from the flow limitation parameter values for a certain number of previous breaths, e.g., three, five or ten breaths depending on the type of current breath. Depending on the combination of parameters, the controlled positive pressure is raised or lowered a large (1.0 cm) or small (0.5 cm) step, returned to the value prior to the last change or left unchanged from the last value.

If there has been no change (NC) in the controlled positive pressure for the past interval, the present breath is normal (N) and the majority function is normal, then the controlled positive pressure is lowered by a large step (LOWR LG). If, however, the present breath is intermediate (I) and the majority function is intermediate or flow limited (FL), then the controlled positive pressure is raised by a small step (RAISE SM). Similarly, if the present breath is flow limited, then the controlled positive pressure is raised a small step if the majority function is intermediate and by a large step (RAISE LG) if the majority function is flow limited. Else, no change is made to the controlled positive pressure.

If the controlled positive pressure has been lowered in the past interval, the present breath is normal and the majority function is normal, then the controlled positive pressure is lowered by a large step (LOWER LG). If, however, the present breath is intermediate or flow limited and the majority function is intermediate or flow limited, then the controlled positive pressure is raised to the previous level (RAISE PV). Else, no change is made to the controlled positive pressure.

If the controlled positive pressure has been raised in the past interval, no action is taken for a period of time, e.g., 10 breaths. Then if the present breath is normal and the majority function is normal, the controlled positive pressure is lowered by a small step (LOWR SM). Conversely, if the present breath is intermediate or flow limited, then the controlled positive pressure is raised by a small step if the majority function is intermediate and by a large step if the majority function is flow limited. Else, no change is made to the controlled positive pressure.

In addition, the detection of apneas is used to initiate the decision to raise the controlled positive pressure. If two apneas of a duration of ten seconds or longer occur within one minute, then the controlled positive pressure is raised. If one long apnea having a duration of twenty seconds or longer occurs, then the controlled positive pressure is raised. If an apparent apnea is associated with a very high leak flow, implying a condition of mask disconnect, then the controlled positive pressure is returned to a predetermined or preset pressure.

Alternatively, the controlled positive pressure may be continuously adjusted at a rate set by a slope parameter, e.g., 0.1 cm per two seconds. The slope parameter and its sign would then be updated based on each breath's flow limitation parameter. In no event can the controlled positive pressure be set below the low limit or above the high limit reference values.

Figure 18:
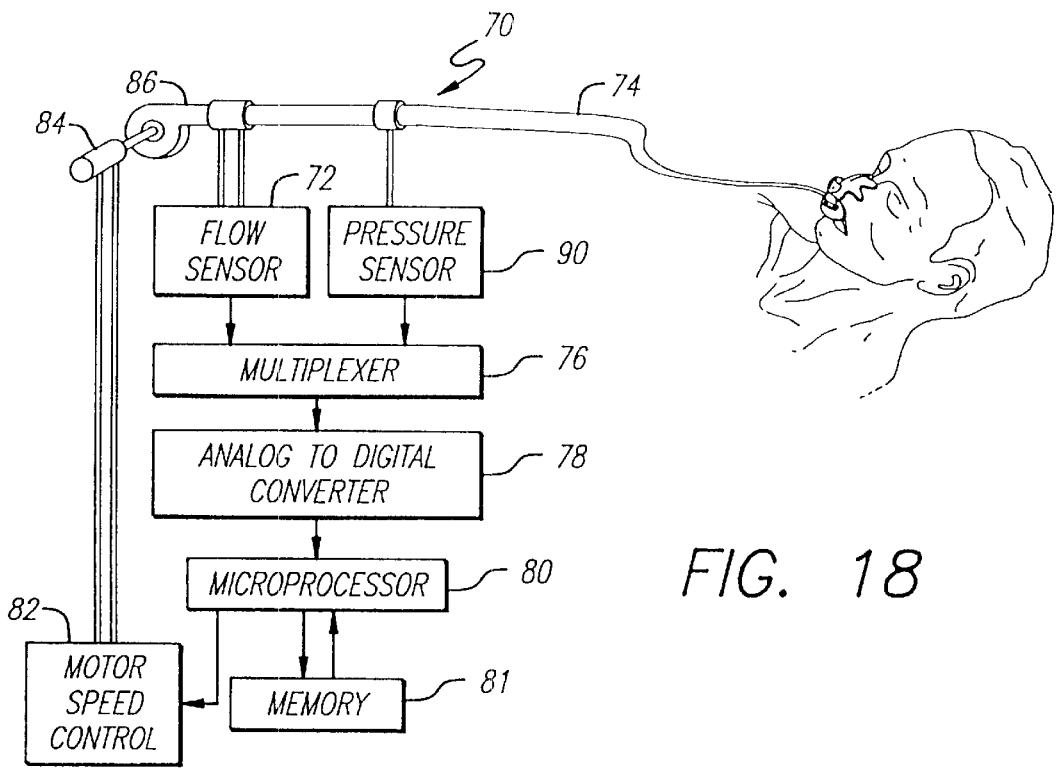
FIG. 18 is a detailed block diagram of a therapeutic apparatus in accordance with the invention.

FIG. 18. shows an alternative therapeutic apparatus in the spirit of the present invention. The breathing device 70 is composed of a flow sensor circuit 72 which senses the flow rate of the breathing gas in the tubing or hose 74 leading to the patient. The flow sensor produces an analog output voltage proportional to the breathing gas flow rate which is conveyed via multiplexer 76 to an analog to digital converter circuit 78 which produces a digital output value which is proportional to the analog voltage output from the flow sensor.

A microprocessor 80 with associated memory 81 and other peripheral circuits executes computer programs which implement the optimizing methods heretofore described. The microprocessor or similar computing device uses the digital output values from a multiplexer 76 and an analog-to-digital converter 78. The microprocessor produces a speed control signal which adjusts a motor speed control circuit 82 which controls the speed of a blower motor 84. Similarly, the variable-speed motor drives the fan blades of a blower 86 which supplies the air flow to the patient through or past the air flow sensor 72. The speed of the blower determines the pressure in the patient circuit. Thus, the microprocessor is able to adjust the pressure of the patient circuit 70 in response to the data values from the flow sensor.

The breathing device 70 may also incorporate a pressure sensor circuit 90 to allow the microprocessor 80 to obtain a direct measurement of the pressure in the patient tubing 74 via the analog to digital converter circuit 78. Such a configuration would allow the microprocessor to maintain the pressure within the maximum and minimum pressure limits established by the prescribing physician. The actual operating pressure levels can be stored in the memory 81 of the microprocessor every few minutes, thus providing a history of pressure levels during the hours of use when the stored data values are read and further processed by a separate computer program.

A signal representative of the speed of the blower could be stored in memory instead of the pressure data values; however, such speed values do not change as rapidly as measured pressure values. If the blower pressure versus speed characteristics are suitable, i.e., approximately constant pressure at a given speed regardless of the air flow rate, then the pressure sensor circuit may be eliminated, thereby reducing the cost to produce the apparatus and making it affordable by a greater number of patients. Alternatively, a patient circuit having a positive pressure breathing gas source and pressure control valve, as disclosed in U.S. Pat. No. 5,065,756, may be used.

Figure 19:
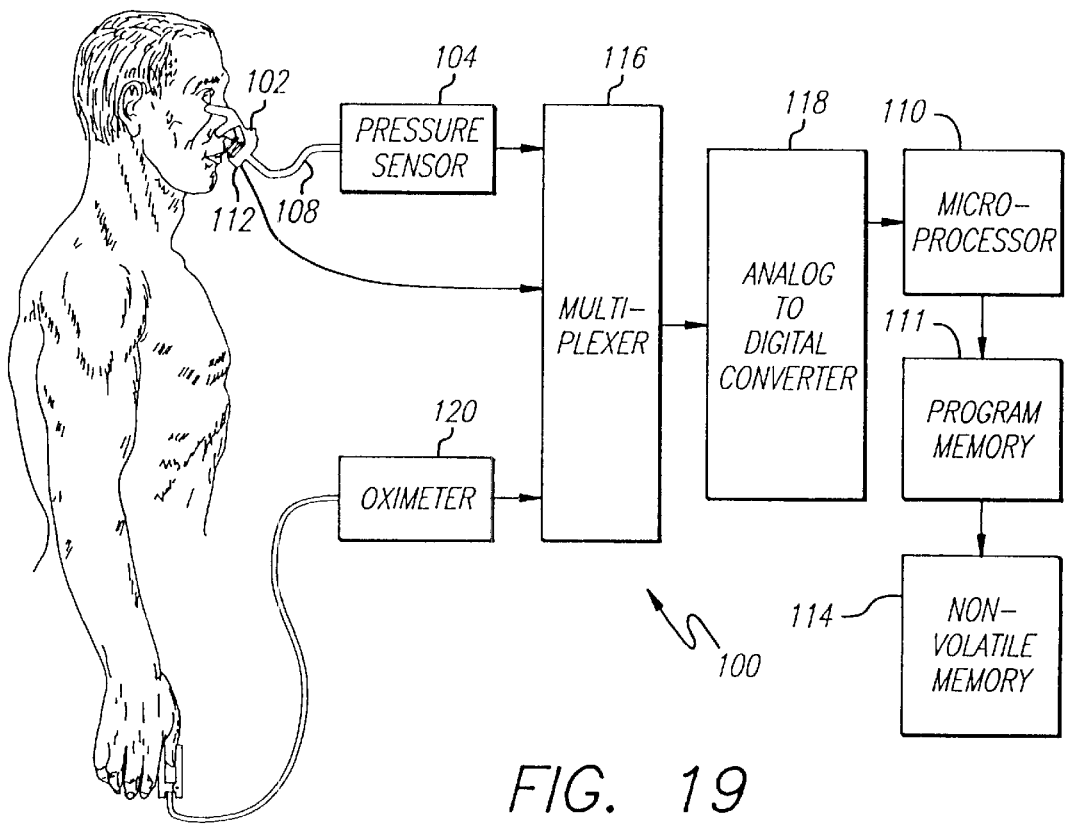
FIG. 19 is a detailed block diagram of a diagnostic system in accordance with the invention.

The methodology for detecting flow limitation can be applied by an automated or manual analysis of the inspiratory flow waveform from the positive pressure generator or from any measurement of the inspiratory flow waveform. Thus the method and apparatus heretofore described may be used for diagnostic purposes in a hospital, sleep lab or the home. Detection and measurement of inspiratory and expiratory flow can be from a standard CPAP system with a flow signal output or by a diagnostic system 100 as shown in FIG. 19. Data values representative of the measured inspiratory and expiratory flow can be logged by a microprocessor 110 in various forms of computer memory 114.

Figure 20:
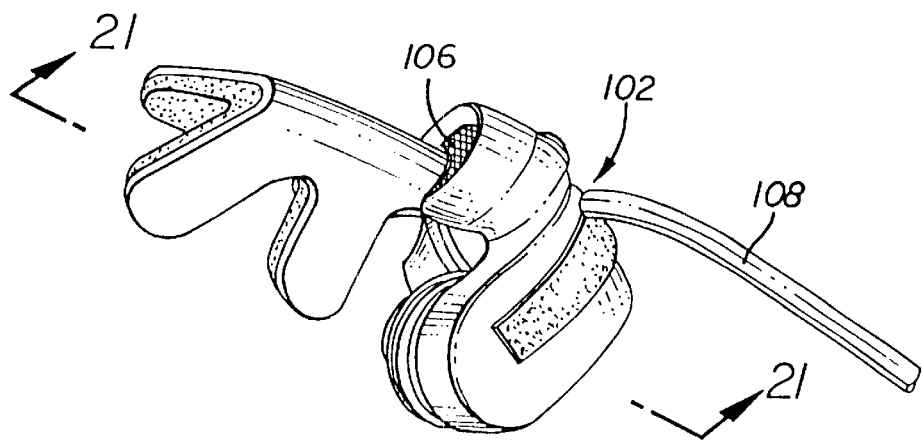
FIG. 20 is a perspective view of a nose fitting for diagnostic use with the method of the present invention.
Figure 21:
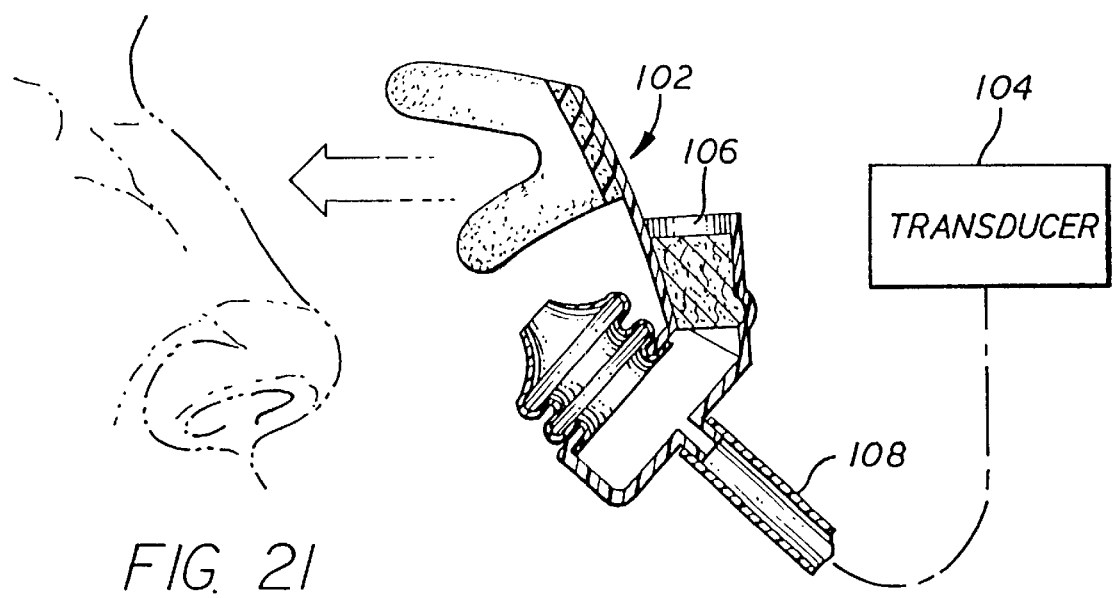
FIG. 21 is a partial cross-sectional view of a nose fitting for diagnostic use with the method of the present invention.

As shown in FIGS. 20 and 21, the detection and measurement of breathing gas flow is made from a tight sealing nose fitting 102 (mask or prongs) configured with a resistive element 106 inserted in the flow stream as breathing gas exits from and enters into the fitting. The nasal fitting is further provided with a port 108 for connection to a flow or pressure transducer 104. The resistive element causes a pressure difference to occur between the upstream side and the downstream side when air flows through the element. The magnitude of the pressure difference is proportional to the magnitude of the flow of the air through the resistive element. By continuously measuring the pressure difference, the measurement of the air flow through the resistive element is effectively accomplished. In the preferred embodiment, the pressure measurement is made between the inside of the nose fitting and the ambient pressure in the room. Additional details regarding the construction of such a nose fitting may be found in U.S. Pat. No. 4,782,832, incorporated herein by reference.

An alternative nose fitting may consist of a tight fitting nasal mask such as that disclosed in U.S. Pat No. 5,065,756.

An improved mask seal may be achieved by using a ring of dual sided adhesive tape formed in a ring or oval along the perimeter of the mask where the nasal mask contacts the patient. In addition, the perimeter of the nasal mask may be configured with a pliable material which would conform to the shape of the face of the patient. A vent and flow restrictor may be configured in the mask and placed in fluid communication with a flow and/or pressure sensor or transducer.

In FIGS. 20 and 21, a nasal prong 102 has been configured with a mesh screen resistor 106 at the air inlet, which creates a pressure signal within the nasal prong proportional to the air flow through the nasal prong. Although the figures show an external pressure transducer 104 coupled to the nose fitting by flexible tubing 108, the pressure transducer could be embedded within the structure of the nose fitting, thereby sensing the pressure difference between the inside and outside of the nose fitting. Pressure and flow data values may be continuously measured and recorded on a data logging device such as a micro-processor 110 having program memory 111 and a storage medium 114. Thus, the recorded flow signal may be analyzed during or after collection to categorize breaths as described heretofore.

Such an analysis can be tabulated in several ways, which permit either diagnosis of subtle elevations of upper airway resistance (not resulting in frank apnea) or to adjust a single prescription pressure of CPAP in a well standardized manner either in the laboratory or on the basis of home studies. Possible tabulations of percent time or numbers of breaths with normal, intermediate, and flow limited contours may include time of night, patient position (which can be recorded simultaneously with a position sensor 112 in the mask or on the patient's body), sleep stage (as recorded separately) and controlled positive pressure.

The controlled positive pressure could be constant throughout the night or varied in several ways to gain diagnostic and therapeutic information of relevance to a patient's condition. For example, the controlled positive pressure could be changed throughout a night manually in the sleep laboratory by a technician. Similarly, the controlled positive pressure could be changed automatically via an automated system, either in response to feedback control or using pre-set ramps or steps in the controlled positive pressure throughout the night (in laboratory or at home). Likewise, the controlled positive pressure could be changed on multiple individual nights, e.g., at home.

As shown in FIG. 18, the flow waveforms may be recorded in a recording device, such as a microprocessor 80 with associated memory 81. As heretofore described, data values may be recorded while the patient is using a self-adjusting controlled positive pressure apparatus described herein. Similarly, data values may be recorded while the patient is connected to a constant-pressure air supply having a flow sensor. Such flow waveforms are obtained at positive airway pressures above ambient pressure. However, to determine the frequency and severity of flow limitations and apnea in a patient who is not receiving therapy, it is necessary to obtain flow waveforms when the patient is breathing at ambient pressure.

FIGS. 19, 20 and 21 illustrate a device of the present invention wherein a nose fitting 102 is used without connection to a breathing gas supply for obtaining flow data values at ambient pressure. The nose fitting is connected to a pressure or flow sensor 104 which supplies data values to a micro-processor 100 via a multiplexer 166 and analog-to-digital converter 118. Software for storing and analyzing the data may be stored in read-only program memory 111, while the data values are stored in random-access memory or non-volatile memory 114. Additionally, an oximeter 120 and/or similar diagnostic devices may be connected to the patient and multiplexer for generating additional data values for use and storage by the microprocessor.

An alternative nasal connection could be achieved by using a "standard" nasal cannula commonly used for supplying supplemental oxygen therapy to patients. Such a cannula does not provide a seal between the nasal prong and the naris, so it does not capture all the air flowing to and from the patient. However, it does capture the small pressure fluctuations in the nares and transmit them to an attached pressure sensor to provide a signal representative of the actual flow waveform shape.

The recording device may be configured with a microprocessor 110 which uses a sample-and-hold circuit, and an analog-to-digital converter 118 to digitize samples of analog voltage signals at a suitable rate and resolution to capture relevant waveform detail, e.g., fifty samples per second rate and resolution of one part in 256 ("eight bit") for breathing flow waveforms. The digitized samples are then stored in time-sequential order in a non-volatile memory device 114, e.g. magnetic disk drive, "flash" memory, or battery-backed random-access memory.

In order to record more than one signal, e.g. flow and pressure waveforms and position signal, in time-correlated sequence, the individual signals can be repetitively sequentially connected to the sample-and-hold circuit by a multiplexer circuit 116. All of these recording device circuit and devices are well known to one skilled in the art of electronic circuit design, and can readily be obtained commercially.

In order to enhance the diagnostic potential of this flow waveform sensing and analyzing technique, the flow sensor 104 could be combined with a position sensor 112 to determine the dependence of position attributes of the flow limitation. Likewise, adding pulse oximetry 120, which measures the oxyhemoglobin saturation level in the patient's blood, to the flow and position measurements would provide a very useful combination of diagnostic signals, adequate to diagnose and document the severity of the upper airway obstructions.

The following describes a method of diagnosing and treating obstructive sleep apnea and upper airway resistance syndrome using the methods and apparatus for determining flow limitation in a patient as heretofore described. At present, a patient seeking physician treatment has symptoms of excessive sleepiness and possibly snoring, in spite of the patient apparently spending enough time in bed to provide adequate sleep. Such symptoms may or may not be indicative of obstructive sleep apnea and require further analysis, typically in an overnight stay in a sleep lab. Under the present invention, the physician provides the patient with a diagnostic device for use during sleep at home. The diagnostic system records flow and pressure waveforms as previously described, using a nose mask, nasal cannula or similar nasal fitting having a flow restrictor and a pressure and or flow transducer.

While the patient is using the diagnostic device at home, the digitized waveforms are stored in nonvolatile memory such as flash memory, floppy or hard disk, or battery-powered random-access memory (RAM). One or two additional measurements may optionally be recorded: patient sleeping position from a position sensor on the patient, and blood oxyhemoglobin saturation level (in percent $SaO_2$) from a device such as a pulse oximeter. Since the value of these two measurements do not change relatively rapidly (one value per second for each additional measurement versus fifty values per second for flow), the memory storage requirements would not be increased significantly.

After using the diagnostic device to record the desired parameters while sleeping for one or more nights, the patient returns the device or data storage unit, e.g., a disk or non-volatile memory card, to the physician. The physician extracts the data from the storage, and analyzes it to determine the amount of flow limitation and apnea present, along with the other two parameters, if they were recorded. The resulting analysis is used to determine whether the patient needs a more detailed sleep study (in a sleep lab or in the home), or whether therapy should be started without further studies.

If the decision is to start therapy because sufficient flow limitation and/or apnea is present, the patient is provided with a self-adjusting therapy device for home use of the method of the present invention described heretofore. The home therapy device also incorporates a recording component which records flow, pressure and one or two optional parameters as described above. After using this therapy device during sleep for one or more nights, the data is returned to the physician. The physician analyzes it to document the reduction of flow limitation and apnea achieved by the therapy device, to document the reduction in $SaO_2$ desaturations if the optional parameter was recorded, and to determine whether the patient's condition could be effectively treated by a less expensive therapy device which is not self-adjusting, for example standard continuous positive airway pressure.

The patient is then given the appropriate therapy device, or, if anomalies in the breathing pattern are observed during the recorded therapy nights, the patient may be referred for a more extensive sleep study. After the patient has been using the therapy device for several weeks or months, a repeat use of the self-adjusting therapy device with recording component for a follow-up study should be accomplished. The data are analyzed as above, and the appropriate actions taken.

FIG. 22 shows a method of diagnosing and treating a patient who reports excessive sleepiness and perhaps also snoring. Initially at step 150, the patient reports being excessively sleepy and possibly having snoring episodes, perhaps raucous, raspy snoring with abrupt interruptions of the snoring sounds characteristic of obstructive apneic episodes. At step 152, the patient is instructed how to use the diagnostic device and how to position the sensor(s). The diagnostic device collects flow data, and optionally, position and/or oximetry data. The data is collected at a rate sufficiently high to capture the details of each waveform. For flow, a rate of fifty samples per second is appropriate, while position and oximetry only require one sample per second each. The data file also contains information to correlate the data with time and date, so sleeping patterns can be ascertained.

Prior to the period of diagnostic sleep, the patient puts on the sensor(s), turns on the diagnostic device, and goes to sleep. When the patient awakes in the morning, the patient turns the diagnostic device off. During the period of sleep, the diagnostic device collects the data as described above. If the diagnostic procedure is to be a multi-night period of sleep, then the patient repeats this data collection phase for however many nights are required. At step 154, and after the required number of nights of data collection, the patient returns the diagnostic device with the stored data. If the study will be extended, then the patient removes the data storage module and returns only the module to the physician.

The stored data are analyzed at step 156 to determine the amount and severity of flow limitation, and the number and severity of apneas, if any. This analysis can be performed either manually, or preferably by an automated process such as the methods for determining flow limitation as described heretofore. At step 158, a decision is then made as to whether the patient has flow limitation. If there is no evidence of flow limiting or apnea in the stored data, then the patient is referred at step 160 to a sleep lab for a more comprehensive study to determine whether the patient has other problems such as restless legs syndrome, etc.

If flow limitation is present, or apneas are found, then the patient is instructed how to use the self-adjusting controlled positive pressure therapy device, step 162. The therapy device is equipped with a module which collects and stores flow and pressure data, along with the (optional) position and oximetry data, as described above. Note that this step includes collecting data from a pressure sensor measuring the pressure at the airflow outlet of the therapy device. Such pressure data could also be obtained from a pressure sensor connected to the patient attachment device (ADAM shell or nasal mask, etc.). Although less desirable because of the uncertainty of actual pressure at the patient, the pressure data could be replaced by data representing the blower speed, if the therapy device adjusts pressure by changing blower speed. The patient sleeps at home with the therapy device for the required number of nights. During each night, the therapy device collects and stores the data as described above.

At step 164, the patient returns the therapy device or its data storage module for analysis of the stored data after the required number of nights of data collection. Then, the stored flow data are analyzed at step 166 to determine the amount and severity of flow limitation, and the number and severity of apneas, if any exist. The flow limitation analysis can be performed either manually, or preferably by an automated process such as by the methods described heretofore. The stored pressure data are analyzed at step 168 to determine the pressure required to alleviate flow limitations and apneas, and the distribution of required pressures during the diagnostic period of sleep. When the pressure data values are collected from the outlet of the therapy device, then the data values can be corrected to reflect the estimated pressure at the nasal fitting if the resistance of the hose or tubing between the outlet and the nasal fitting is known. For example, $$P_{nose} = P_{outlet} - FLOW*RESISTANCE.$$

At step 170, a decision is made whether the analysis determines that there are still a significant number of sleep-disordered breathing episodes during the night, and/or that the therapy device is incapable of alleviating such episodes at its highest pressure limit. Such a limit may have been selected by the prescribing physician at a level less than the maximum capability of the therapy device. If the therapy device did not restore normal breathing, then the patient is referred to a sleep lab for a more comprehensive study, step 160.

If the therapy device restores normal breathing patterns for the patient, the pressure data are reviewed at step 172 for the proper prescription of a controlled positive pressure therapy device. If the peak therapy pressures fluctuate significantly, then the patient is provided with a prescription for a self-adjusting controlled positive pressure therapy device for continued home use, step 174. To reduce patient cost, such a device would not necessarily incorporate the data storage capabilities of the therapy device used for the previous steps in this method. If, however, the pressure data show consistent night-to-night peak pressures, and the maximum pressure used to alleviate sleep-disordered breathing events is relatively low, e.g., eight centimeters of water pressure or less, then the patient would be prescribed conventional CPAP. (non-self-adjusting) therapy, step 176.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. An apparatus for the treatment of an obstruction in the airway of a patient, comprising:

a source of breathing gas configured to provide breathing gas flow to a patient and to provide positive pressure in the airway of the patient;

a sensor to detect the flow of the breathing gas to the patient;

a signal processor operatively connected to the sensor and configured to define a waveform contour of an inspiratory flow of the breathing gas to the patient, and further configured to utilize the waveform contour to detect the presence or absence of an obstruction in the airway of the patient; and a controller operatively connected to the signal processor, the controller being configured to adjust the positive airway pressure to the patient when the signal processor detects the presence or absence of an obstruction in the airway of the patient.

2. The apparatus of claim 1, wherein the controller is further configured to increase the airway pressure when the signal processor detects the presence of an obstruction, and the controller is further configured to decrease the airway pressure when the signal processor detects the absence of an obstruction.

3. An apparatus for optimizing the positive pressure in an airway of a patient, comprising:

means for providing positive pressure of a breathing gas to an airway of a patient;

means for generating a signal corresponding to a waveform contour of an inspiratory flow of breathing gas to the patient;

means for utilizing the wave form contour signal to detect a flow limitation in the airway of the patient; and means for increasing the positive airway pressure when the means for utilizing detects a flow limitation in the airway of the patient.

4. The apparatus of claim 3, further including means for decreasing the positive airway pressure when the means for utilizing does not detect a flow limitation in the airway of the patient.

5. The apparatus of claim 4, wherein the means for utilizing is configured to generate data values representative of the signal corresponding to the inspiratory flow, to correlate the data values with a pure sine wave to determine a first index, to compare a regression fit of the data values with a regression fit of a pure sine wave to determine a second index, to compare a peak value of the data values with a peak value of a derivative of the data values to determine a third index, and to compare a peak value of the data values with an average of a plurality of peak flow values for flow limited breaths and with an average of a plurality of peak flow values for non-flow limited breaths to determine a fourth index.

6. The apparatus of claim 5, wherein the means for utilizing is further configured to determine a fifth index as a function of the first index, the second index, the third index and the fourth index, wherein each index includes a weighted coefficient.

7. The apparatus of claim 3, wherein the means for utilizing is configured to generate data values representative of the signal corresponding to the inspiratory flow, to correlate the data values with a sinusoidal contour, to analyze the data values for flatness, to analyze the data values for respiratory effort, and to analyze the data values for relative flow magnitude.

8. An apparatus for optimizing the positive pressure in an airway of a patient, comprising:

a source of positive pressure of breathing gas provided to an airway of a patient;

a first sensor configured to generate a first signal corresponding to a waveform contour of an inspiratory flow of breathing gas to the patient;

a memory device configured to store the first signal generated by the first sensor;

a microprocessor configured to utilize the first signal to generate a second signal indicative of a flow limitation in the patient; and a controller operably connected to the source of breathing gas and responsive to the second signal from the microprocessor so as to increase the positive pressure of the breathing gas in response to the second signal.

9. The apparatus of claim 8, wherein the microprocessor is further configured to generate a third signal when the first signal does not indicate a flow limitation in the patient, and wherein the controller is further configured to decrease the positive pressure of the breathing gas in response to the third signal.

10. The apparatus of claim 8, wherein the microprocessor is further configured to correlate the first signal with a pure sine wave.

11. The apparatus of claim 8, wherein the microprocessor is further configured to compare a regression fit of the first signal with a regression fit of a pure sine wave.

12. The apparatus of claim 8, wherein the microprocessor is further configured to compare a peak value of the first signal with a peak value of a derivative of the first signal.

13. The apparatus of claim 8, wherein the microprocessor is further configured to determine a plurality of peak flow values for flow limited breaths, to determine a plurality of peak flow values for non-flow limited breaths, and to compare a peak value of the first signal with an average of the plurality of peak flow values for flow limited breaths and with an average of the plurality of peak flow values for non-flow limited breaths.

14. A method for optimizing the positive pressure in an airway of a patient, comprising:

providing air at positive pressure to an airway of a patient;

monitoring the flow of air to the patient;

defining an inspiratory waveform contour of the flow of air to the patient;

analyzing the inspiratory waveform contour to determine the presence or absence of a patient airway obstruction; and adjusting the positive pressure of air to the patient in response to the presence or absence of a patient airway obstruction.

15. The method of claim 14, wherein adjusting the positive pressure of air to the patient includes increasing the positive pressure of air to the patient when the inspiratory waveform contour indicates a patient airway obstruction, and further includes decreasing the positive pressure of air to the patient when the inspiratory waveform contour does not indicate a patient airway obstruction.

16. A method for optimizing the positive pressure of breathing gas to an airway of a patient, comprising:

applying breathing gas at positive pressure to an airway of a patient;

detecting an inspiratory flow of breathing gas to the patient;

generating a signal corresponding to a waveform contour of the inspiratory flow of breathing gas to the patient;

determining whether the waveform contour signal indicates a flow limitation in the airway of the patient; and increasing the positive pressure of breathing gas when the signal indicates a flow limitation in the airway of the patient.

17. The method of claim 16, further comprising decreasing the positive airway pressure when the signal does not indicate a flow limitation in the airway of the patient.

18. The method of claim 17, further comprising:

calculating a first index by comparing the signal with a pure sine wave;

calculating a second index by comparing a regression fit of the signal with a regression fit of a pure sine wave;

calculating a third index by comparing a peak value of the signal with a peak value of a derivative of the signal;

determining peak flow values for a plurality of flow limited breaths;

determining peak flow values for a plurality of non-flow limited breaths; and calculating a fourth index by comparing a peak value of the signal with an average of the peak flow values for the plurality flow limited breaths and with an average of the peak flow values for the plurality of non-flow limited breaths.

19. The method of claim 17, wherein determining whether the signal indicates a flow limitation in the airway of the patient further includes calculating a fifth index as a function of the first index, the second index, the third index and the fourth index, wherein the fifth index indicates the presence of flow limitation in the patient.

20. The method of claim 17, wherein determining whether the signal indicates a flow limitation in the airway of the patient further includes calculating a fifth index as a function of the first index, the second index, the third index and the fourth index, wherein the function includes a weighted coefficient for each of the first, second, third and fourth indexes.

* * * * *

UNITED STATES PATENT AND TRADEMARK OFFICE
CERTIFICATE OF CORRECTION

PATENT NO. : 6,488,634 B1
DATED : December 2, 2002
INVENTOR(S) : David M. Rapoport and Robert G. Norman It is certified that error appears in the above-identified patent and that said Letters Patent is hereby corrected as shown below:

Column 10,
Line 10, in the equation, change "$B_1+B_0*X_1$", to read -- $B_0+B_1*X_1$ --.

Column 18,
Line 20, change "first signal," to read -- waveform contour signal --.

Column 20,
Lines 13 and 19, change "17", to read -- 18 --.

Signed and Sealed this

Twentieth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,488,634 B1
DATED : December 3, 2002
INVENTOR(S) : David M. Rapoport and Robert G. Norman It is certified that error appears in the above-identified patent and that said Letters Patent is hereby corrected as shown below:

Column 10,
Line 10, in the equation, change "$B_1+B_0*X_1$", to read -- $B_0+B_1*X_1$ --.

Column 18,
Line 20, change "first signal," to read -- waveform contour signal --.

Column 20,
Lines 13 and 19, change "17", to read -- 18 --.

This certificate supersedes Certificate of Correction issued April 20, 2004

Signed and Sealed this

Twenty-ninth Day of June, 2004

JON W. DUDAS
*Acting Director of the United States Patent and Trademark Office*